US012636029B2

(12) United States Patent (10) Patent No.: US 12,636,029 B2

Hafner et al. (45) Date of Patent: May 26, 2026

(54) SURGICAL INSTRUMENT HAVING A BLOCKING MEANS

(71) Applicant: Aesculap AG, Tuttlingen (DE)

(72) Inventors: Nikolaus Hafner, Tuttlingen (DE); Eugen Herner, Villingen-Schwenningen (DE); Hannes Kizenberger, Immendingen (DE); Erik Walberg, Augsburg (DE)

(73) Assignee: Aesculap AG, Tuttlingen (DE)

( * ) Notice: Subject to any disclaimer, the term of this patent is extended or adjusted under 35 U.S.C. 154(b) by 416 days.

(21) Appl. No.: 18/028,861

(22) PCT Filed: Sep. 27, 2021

(86) PCT No.: PCT/EP2021/076463

§ 371 (c)(1),
(2) Date: Mar. 28, 2023

(87) PCT Pub. No.: WO2022/069393

PCT Pub. Date: Apr. 7, 2022

(65) Prior Publication Data

US 2023/0329737 A1     Oct. 19, 2023

(30) Foreign Application Priority Data

Sep. 29, 2020    (DE) ..................... 10 2020 212 252.0

(51) Int. Cl.
*A61B 17/28*         (2006.01)
(52) U.S. Cl.
CPC ................................ *A61B 17/2833* (2013.01)
(58) Field of Classification Search
CPC ............ A61B 17/2909; A61B 17/2946; A61B 2017/2833; A61B 2017/32113; B25B 7/14
See application file for complete search history.

(56) References Cited

U.S. PATENT DOCUMENTS

| | | | | | |
|---|---|---|---|---|---|
| 5,626,596 | A | * | 5/1997 | DeSatnick | ......... A61B 17/3211 606/167 |
| 2007/0179524 | A1 | * | 8/2007 | Weber | .................... A61B 17/00 606/205 |
| 2007/0299469 | A1 | | 12/2007 | Carpenter et al. | |

FOREIGN PATENT DOCUMENTS

| | | | |
|---|---|---|---|
| DE | 102008017299 | A1 | 10/2009 |
| DE | 102016117052 | A1 | 3/2018 |

(Continued)

OTHER PUBLICATIONS

Search Report in International Application No. PCT/EP2021/076463, dated Jan. 12, 2022, 5 pages.

*Primary Examiner* — Katherine H Schwiker

(74) *Attorney, Agent, or Firm* — Christopher A. Rothe; CM Law

(57) ABSTRACT

A surgical instrument and use of a surgical instrument in open surgery. The instrument has two gripping limbs and a blocking element that releasably locks the gripping limbs relative to one another. The blocking element has a female locking assembly and a male locking assembly. The female locking assembly has a mechanical control device for locking and releasing a locking portion of the male locking assembly. A mechanical control assembly is assigned to the male locking assembly and moves the locking portion of the male locking assembly out of an end position that defines a neutral position into an end position that defines a functional position and, conversely, out of the end position that defines the functional position into the end position that defines the neutral position. The control assembly includes securing elements that secure the locking portion in both end positions.

5 Claims, 11 Drawing Sheets

(56)    References Cited

FOREIGN PATENT DOCUMENTS

Figure 1:
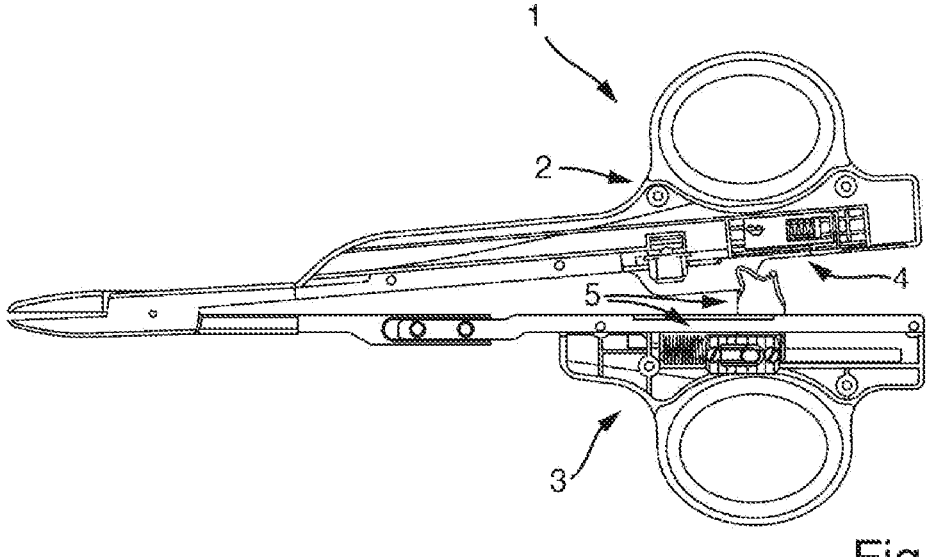

| | | | | |
|---|---|---|---|---|
| DE | 102016118119 | A1 | | 3/2018 |
| DE | 102016118199 | A1 * | 3/2018 | ............ A61B 90/03 |
| EP | 513471 | A2 | | 11/1992 |
| EP | 1849420 | A1 | | 10/2007 |

* cited by examiner

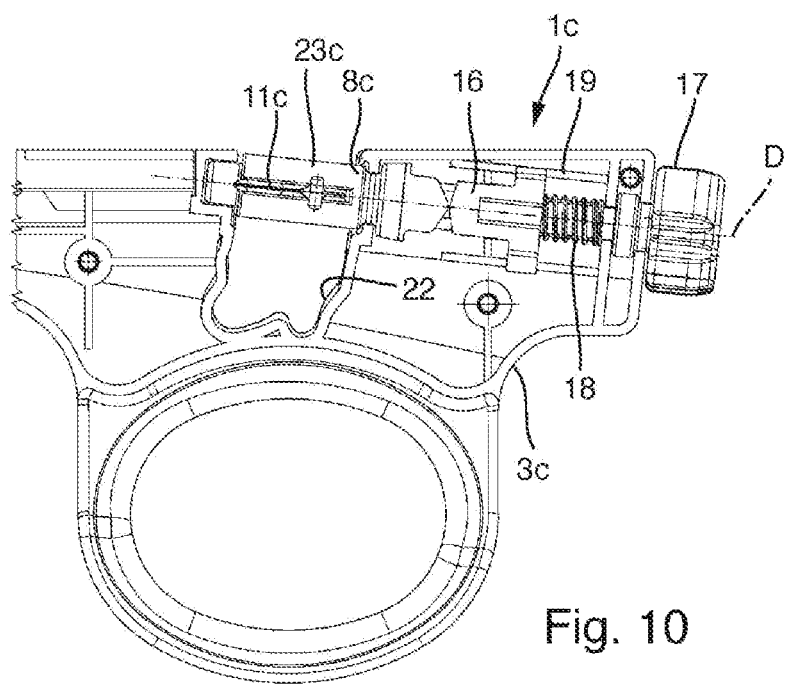
Fig. 10
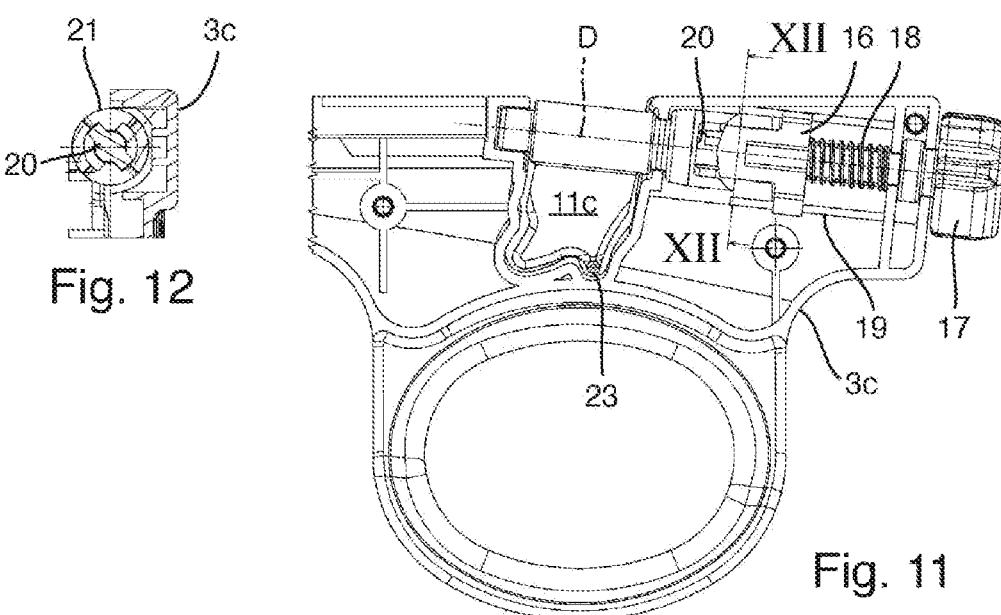
Fig. 12
Fig. 11

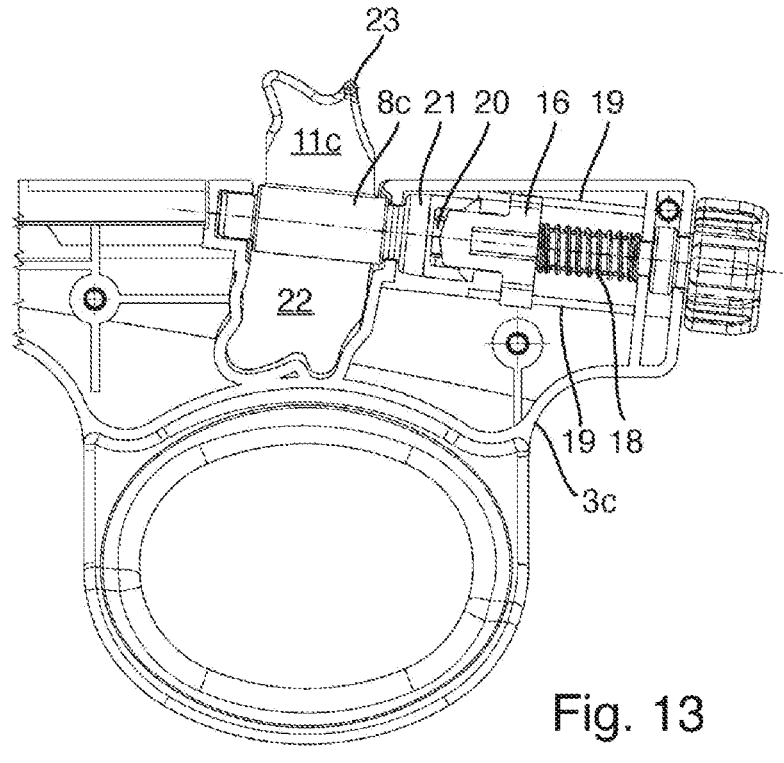
Fig. 13
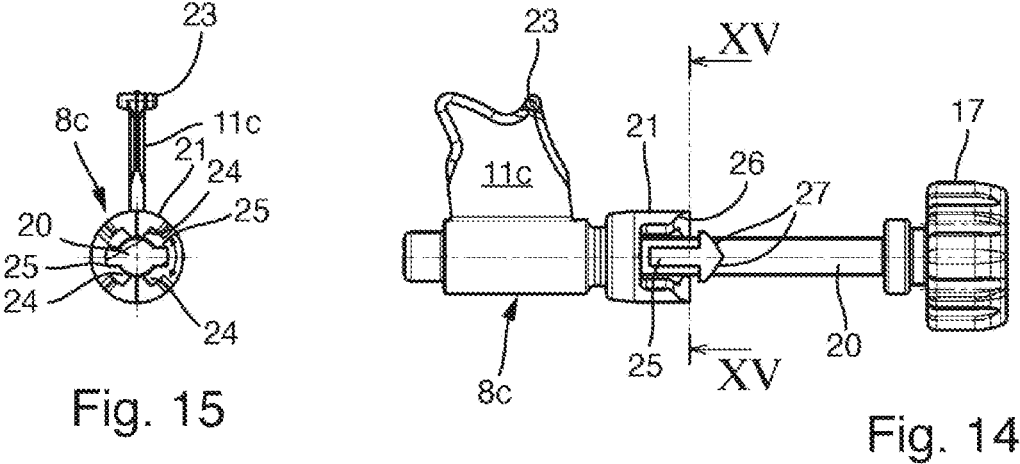
Fig. 15
Fig. 14

1

SURGICAL INSTRUMENT HAVING A BLOCKING MEANS

CROSS-REFERENCE TO RELATED APPLICATIONS

This application is the United States national stage entry of International Application No. PCT/EP2021/076463, filed Sep. 27, 2021, and claims priority to German Application No. 10 2020 212 252.0, filed Sep. 29, 2020. The contents of International Application No. PCT/EP2021/076463 and German Application No. 10 2020 212 252.0 are incorporated by reference herein in their entireties.

FIELD

The invention relates to a surgical instrument having two gripping limbs, which can be moved relative to one another, and having a catch, which is provided to arrest the two gripping limbs relative to one another in a releasable manner, wherein the catch has a female arresting arrangement in the region of the one gripping limb and a male arresting arrangement in the region of the other gripping limb, wherein the female arresting arrangement has a mechanical control device for arresting and freeing an arresting portion of the male arresting arrangement.

BACKGROUND

Such a surgical instrument is known from DE 10 2016 118 199 A1. The known surgical instrument is designed in the form of a clamping instrument in which the two gripping limbs extend, distally, into clamping jaws which, by the gripping limbs being moved relative to one another, are moved apart from one another or guided together for clamping purposes. The known clamping instrument has a catch, which arrests the gripping limbs relative to one another in a releasable manner, so that a clamping state of the clamping jaws can be maintained. The catch has a male arresting arrangement on the one gripping limb and a female arresting arrangement on the opposite gripping limb, as seen in relation to a pivoting plane of the gripping limbs. The male arresting arrangement is provided with an arresting portion which projects toward the opposite gripping limb and is mounted such that it can be slid in translatory fashion along the gripping limb. The female arresting arrangement, which is provided on the opposite gripping limb, is intended to accommodate the arresting portion of the male arresting arrangement with form-fitting latching action and has a control track, which is mounted for linear movement along the associated gripping limb and, in accordance with a ballpoint-pen principle, accommodates the arresting portion of the opposite male arresting arrangement, secures the same and frees it again in dependence on corresponding relative movements of the two gripping limbs. During a closing movement of the gripping limbs relative to one another, the arresting portion penetrates into the control track, which can be moved under spring loading. Subsequent removal of loadings from the manual closing movement applied to the two gripping limbs results in the arresting portion latching within the control track of the female arresting arrangement. Renewed pushing together of the gripping limbs by subjecting the latter to manual loading results in the arresting portion being released from the control track of the female arresting portion.

SUMMARY

The object of the invention is to create a surgical instrument of the type mentioned in the introduction which allows the two gripping limbs to be arrested and freed, relative to one another, in a particularly reliable and secure manner.

This object is achieved in that the male arresting arrangement is assigned a mechanical control arrangement, which is provided to displace the arresting portion of the male arresting arrangement from an end position which defines a rest position into an end position which defines a functional position and, vice versa, from the end position which defines the functional position into the end position which defines the rest position, and in that the control arrangement has securing means, which are provided to secure the arresting portion in the two end positions. The solution according to the invention ensures that the arresting portion is always located in a defined end position. The invention avoids undefined intermediate positions, which in the prior art have been able to result in it not being possible for the catch to be arrested in a reliable manner. The mechanical control arrangement can have a spring device in order to transfer the arresting portion of the male arresting arrangement into an end position. The spring device can also serve as a securing means in order to secure the arresting portion in the end position. The securing means are preferably of mechanical design. As an alternative, these securing means can also be active by way of an electromagnet or permanent magnet. The arresting portion can be displaced in translatory or rotary fashion between its end positions. The solution according to the invention is particularly advantageously suitable for open surgical instruments. The surgical instrument preferably has clamping jaws which can be moved by means of the gripping limbs. It is possible to supply power to the clamping jaws. The mechanical control arrangement can be assisted by an electric drive in order to activate or deactivate the catch.

One configuration of the invention provides a manually operable actuating device, which is in operative connection with at least one securing means in order to activate the at least one securing means so as to free displacement capability of the arresting portion. It is thus possible for the mechanical control arrangement to be activated manually, if required, by an appropriate user. Without manual activation, the male arresting portion remains in a defined end position, so that either arresting action with the female arresting arrangement is possible or interaction with the female arresting arrangement is ruled out, depending on whether the male arresting portion is located in the end position which defines the functional position (arresting position) or in the end position which defines the rest position.

In a further configuration of the invention, the arresting portion is guided in translatory fashion along a linear guide for displacement between the two end positions. The linear guide preferably extends in the longitudinal direction of the gripping limb along an edge region of this gripping limb that is directed toward the opposite gripping limb. The linear guide is preferably of rectilinear design, but, as an alternative, can also extend along a curved path in the region of the gripping limb. It is possible for the linear guide to be integrated in one piece in the gripping limb or to be provided in a separately produced carrier part, which, in an operating state, has been fixed to the gripping limb.

In a further configuration of the invention, the linear guide runs along a curved path, in particular along a circle arc. The curved path, in particular the circle arc, extends in the pivoting plane of the gripping limb. The linear guide is preferably designed such that, in its end position which defines the rest position, the arresting portion is positioned within corresponding outer contours of the gripping limb, so that, in this rest position, the arresting portion does not project outward beyond the gripping limb. This reliably avoids the situation where in particular a glove worn by a person operating the surgical instrument gets caught on the arresting portion when the person is handling the instrument.

In a further configuration of the invention, at least one securing means is designed in the form of a force-fit-action securing unit. The force-fit-action securing unit preferably has complementary frictional portions in a fixed position in the region of the gripping limb, on the one hand, and in a movable state on the arresting portion, on the other hand, in particular in the form of a stud-like profiling, on the one hand, and of a recessed profiling, on the other hand. The force-fit-action securing unit is advantageously configured such that it can be released at certain force limits. The securing unit is thus active under certain force limits. As soon as a displacement force applied to the arresting portion is higher than the force which restrains the securing unit in the corresponding end position, the arresting portion is freed for transfer into the correspondingly other end position. The force-fit-action securing unit can also have a permanent magnet or an electromagnet.

In a further configuration of the invention, at least one securing means is designed in the form of a form-fit-action securing unit. The form-fit-action securing unit has a release mechanism, which frees the arresting portion if required.

In a further configuration of the invention, the form-fit-action securing unit is assigned the manually operable actuating device in order for the securing unit to be transferred from a securing position into a freeing position. The manually operable actuating device can have a release mechanism along the lines of the above-described configuration. The manually operable actuating device preferably has at least one operating element, which is positioned in an ergonomically advantageous manner in the region of one of the gripping limbs. In addition, or as an alternative, it is designed so as to remain unaffected by soiling. The manually operable actuating device is preferably designed such that it can be operated in a straightforward and ergonomically advantageous manner both by left-handed people and by right-handed people.

In a further configuration of the invention, the form-fit-action securing unit is configured in a mirror-symmetrical manner relative to a displacement plane of the securing unit, wherein the securing unit has, in particular on opposite sides of the gripping limb, a respective elastically movable latching element, and these latching elements interact with fixed-position latching apertures in the region of the gripping limb. The securing unit is preferably configured in a mirror-symmetrical manner in relation to a pivoting plane of the gripping limbs. The mirror-symmetrical arrangement of two elastically movable latching elements allows the translatory-movement arresting portion to be arrested particularly securely in the corresponding end position. The latching elements are preferably in operative connection with the manually operable actuating device.

In a further configuration of the invention, the arresting portion is guided in rotary fashion by way of a rotary bearing means. The rotary bearing means preferably has an axis of rotation which extends in the longitudinal direction of the gripping limb and therefore at least largely parallel to an edge region of the gripping limb that is adjacent to the opposite gripping limb. The rotary guidance of the arresting portion means that, in the functional position, the arresting portion can be positioned so as to project from the gripping limb and, in the rest position, the arresting portion can be parked within an outer contour of the associated gripping limb.

In a further configuration of the invention, the gripping limb has at least one aperture in which the arresting portion is accommodated in the rest position. The arresting portion is preferably accommodated flush in the aperture. The at least one aperture can be designed in the form of a depression which is at least partially closed on one side, in particular in the form of a pocket or a similar depression which does not pass all the way through the gripping limb, or else in the form of a through-passage, which is open toward both sides of the gripping limb. Depending on the configuration of the at least one aperture, it is therefore possible for the arresting portion to rotate by less than 360° or by 360° and more. Since the arresting portion can be rotated into a rest position, in which the arresting portion does not project beyond the associated gripping limb, the situation where in particular a glove worn by a person operating the surgical instrument unintentionally gets caught on the arresting portion is reliably avoided.

In a further configuration of the invention, the gripping limb has a through-passage, which is coordinated with external dimensions of the arresting portion and is configured such that the arresting portion can rotate through the through-passage in opposite directions of rotation. This means that it is possible for the arresting portion to be transferred not just in one direction of rotation, but in both directions of rotation, from the rest position into the functional position, or vice versa. This configuration is advantageous from an ergonomic point of view since straightforward operation is possible both for left-handed people and for right-handed people, in order to rotate the arresting portion.

In a further configuration of the invention, the arresting portion is assigned a mechanical positive-control device, which provides for unavoidable transfer of the arresting portion from an intermediate position into an end position. The mechanical positive-control device makes it possible, in respect of rotary guidance of the arresting portion, for the arresting portion to be moved automatically, in the event of the positive-control device being appropriately activated, from an intermediate position into the corresponding end position without this being done by manual actuation. This configuration makes it easier for a person operating the surgical instrument to transfer the arresting portion into the corresponding rest position or the corresponding functional position. Malfunctioning or undefined intermediate positions are reliably avoided as a result. The quasi-automatic transfer into the corresponding end position, in addition, reduces the amount of effort which has to be made by the person operating the surgical instrument, and this makes the surgical instrument easier to operate.

In a further configuration of the invention, the positive-control device is interposed between the arresting portion and a manually movable actuating element, in mechanical interaction therewith, such that incipient movement of the actuating element results in the positive-control device being activated. This configuration requires a manually movable actuating element, which initiates a movement into the positive-control device, which is then activated and provides for the desired displacement of the arresting portion into the corresponding end position. The manually movable actuating element is preferably an actuating element which is mounted in rotary fashion in the region of the gripping limb, in particular a rotary knob which is provided with grip surfaces, in particular in the form of ribbing, in the region of its outer circumference in order for the operation of the rotary knob to be simplified. The actuating element is part of the above-described actuating device.

In a further configuration of the invention, the positive-control device has a time-delay unit, which gives rise to a delayed-movement transmission of torque from the actuating element to the arresting portion. This achieves a limited amount of free running, preferably in an angle-of-rotation range between 5° and 85°. In this angle-of-rotation range, it is still the case that actuation of the actuating element does not give rise to any activation of the positive-control device and, in particular, to any transfer of the arresting portion from the one end position into the other end position. The delayed reaction to the arresting portion allows the arresting portion to be secured against unintentional rotation on account of any transverse forces which occur. Accordingly, any transverse forces which act on the arresting portion do not impede the respective end position of the arresting portion. In addition, this configuration is advantageous since relatively small, unintentional rotary movements of the actuating element do not have any effect on the blocking or freeing of the catch.

In a further configuration of the invention, the positive-control device has a plurality of functional components which can be rotated coaxially relative to one another and are provided with control contours which are effective in a direction of rotation and interact with one another for unavoidable transfer of the arresting portion into an end position. Accordingly, the positive-control device acts in rotary fashion, wherein the various functional components at least partially overlap one another preferably in the longitudinal direction of the axis of rotation, this resulting in a space-saving arrangement of the functional components of the positive-control device. The control contours are preferably provided on an inner circumference and/or on an outer circumference of the corresponding functional components, in order to interact with one another in a desired manner in the circumferential direction.

In a further configuration of the invention, the positive-control device has at least one spring device, which applies an activating force to a functional component of the positive-control device. The spring device is advantageously subjected to permanent prestressing. The spring device acts as a spring drive in order for transmission of an initiated rotary movement to a corresponding functional component to be accomplished automatically—that is to say without any manual activity. The spring device can be designed in the form of a constant-force spring or in the form of a progressively active spring device with a spring rate preferably from a range between 0.1 N/mm and 10 N/mm.

BRIEF DESCRIPTION OF THE DRAWING FIGURES

Figure 2:
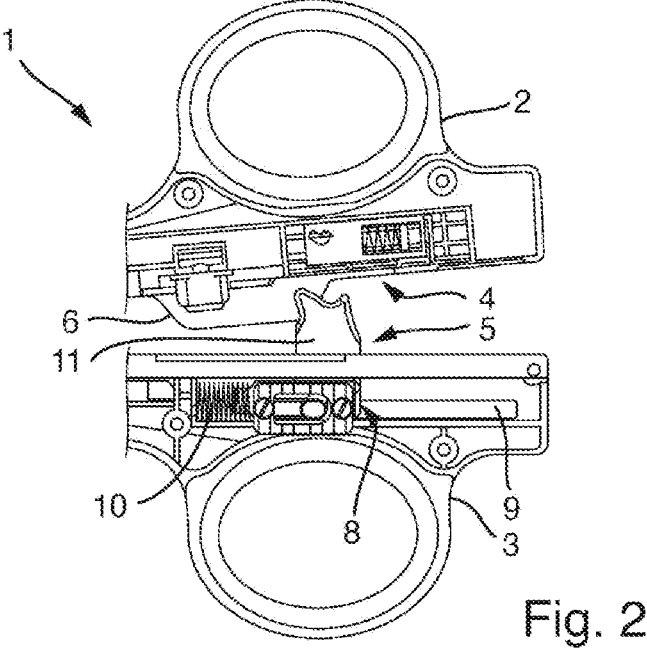
Figure 3:
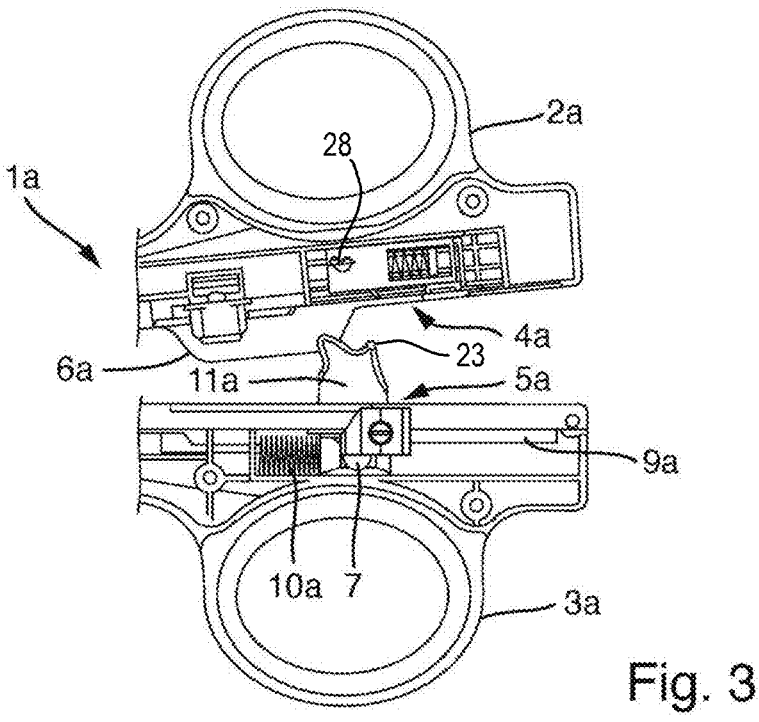
Figure 4:
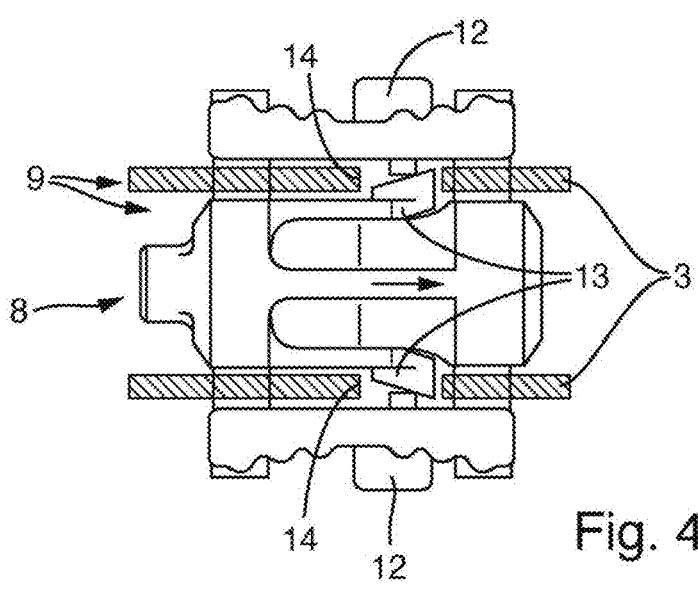
Figure 5:
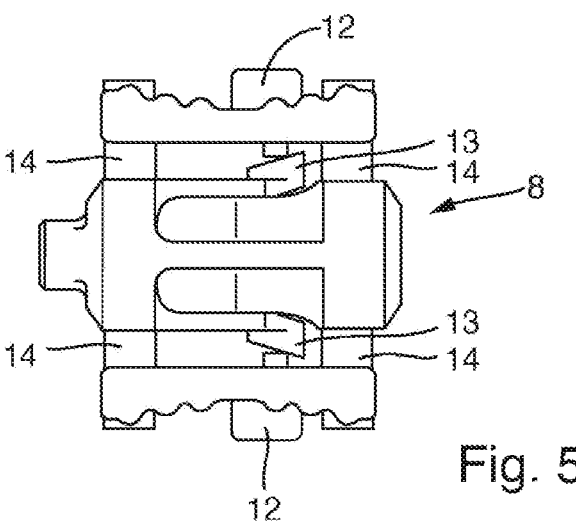
Figure 6:
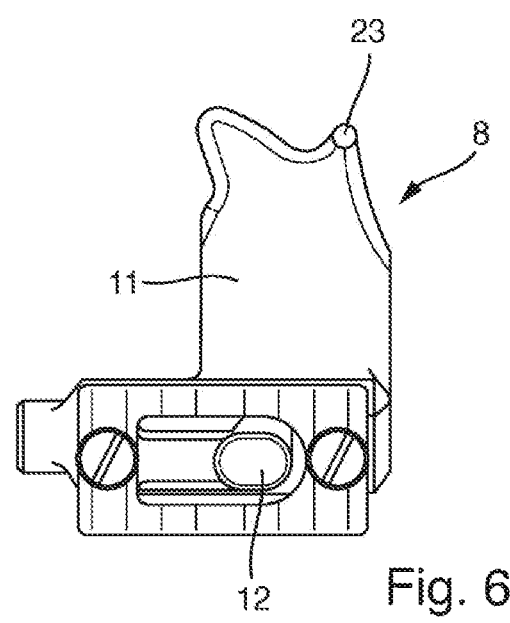
Figure 7:
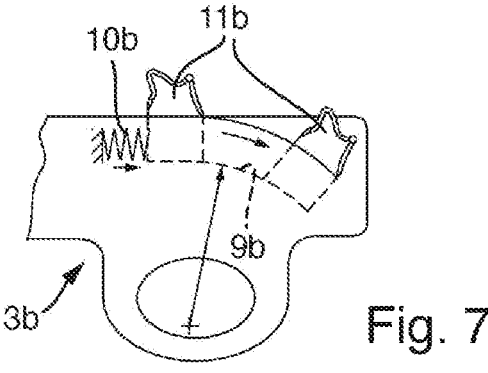
Figure 8:
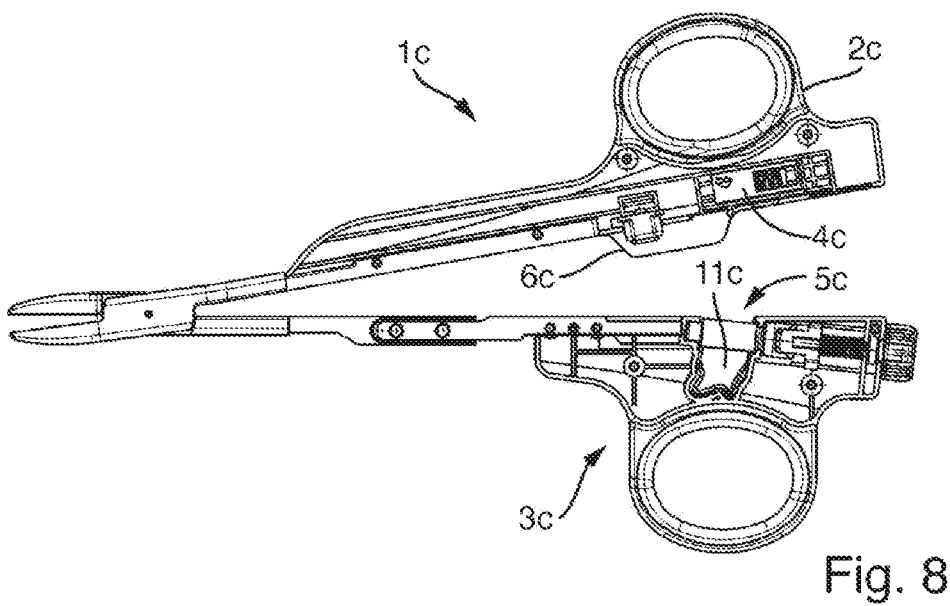
Figure 9:
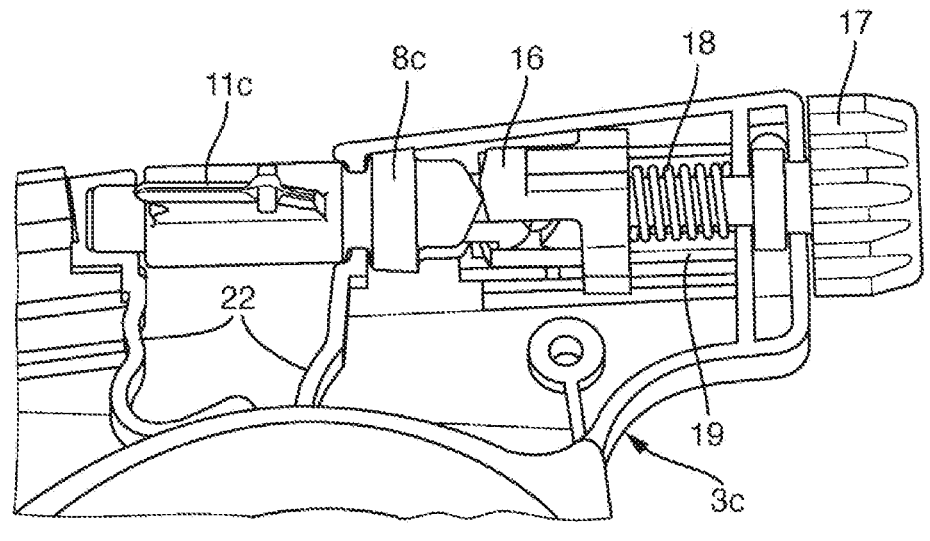
Figure 16A:
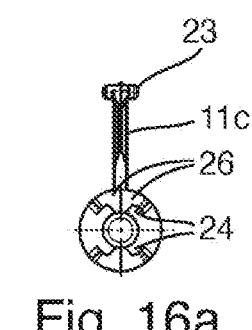
Figure 16B:
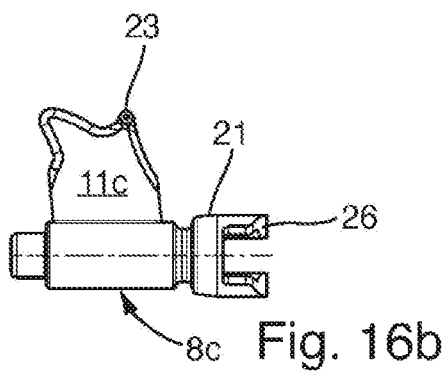
Figure 16C:
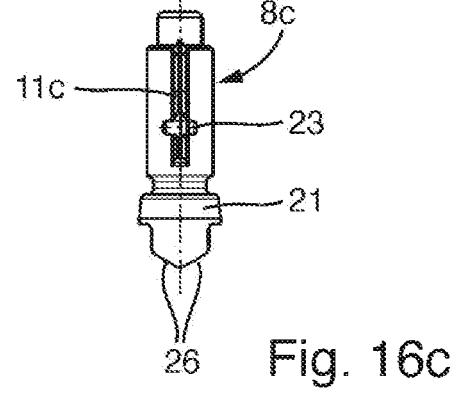
Figure 16D:
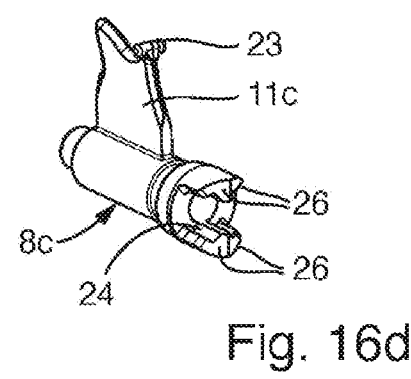
Figure 17A:
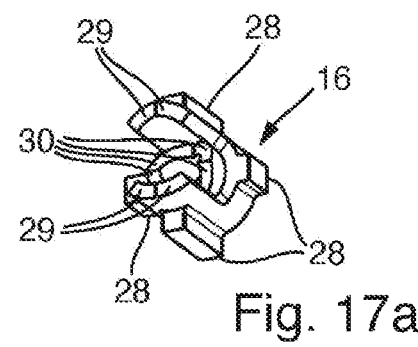
Figure 17B:
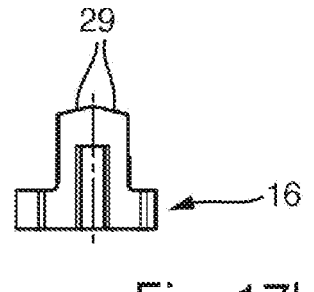
Figure 17C:
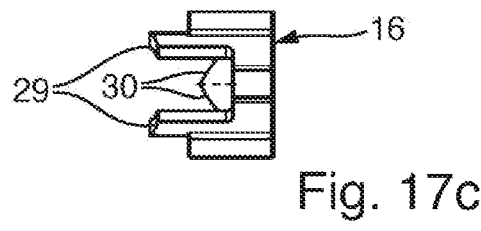
Figure 17D:
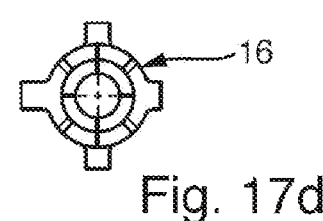
Figure 18A:
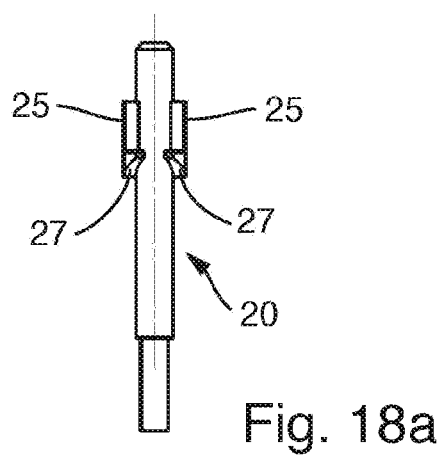
Figure 18B:
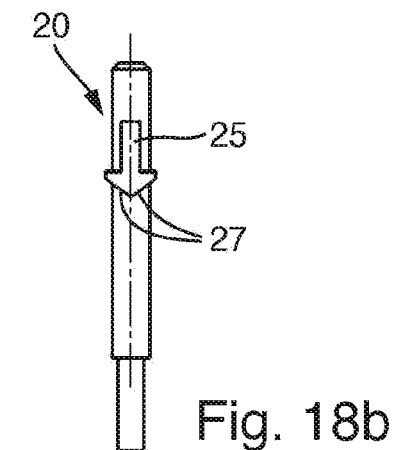
Figure 18C:
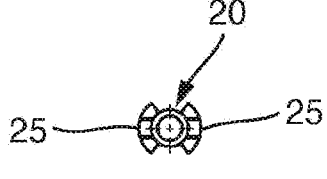
Figure 18D:
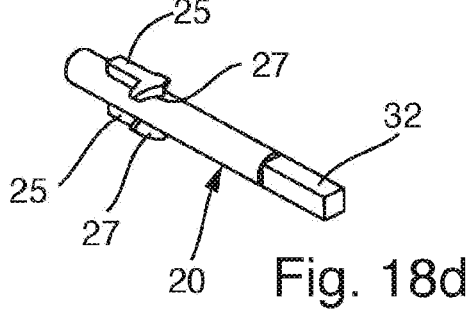
Figure 19A:
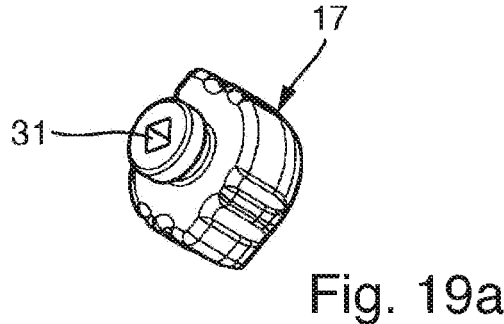
Figure 19B:
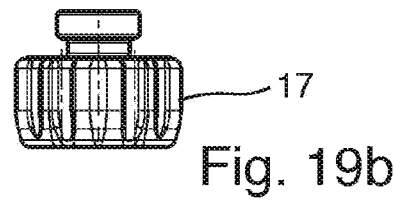
Figure 19C:
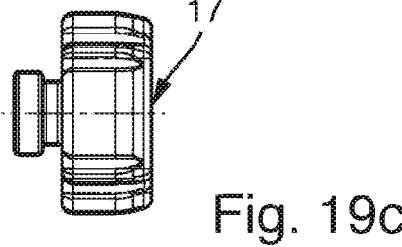
Figure 19D:
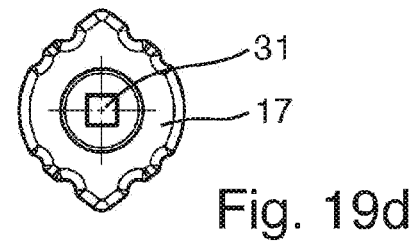
Figure 20:
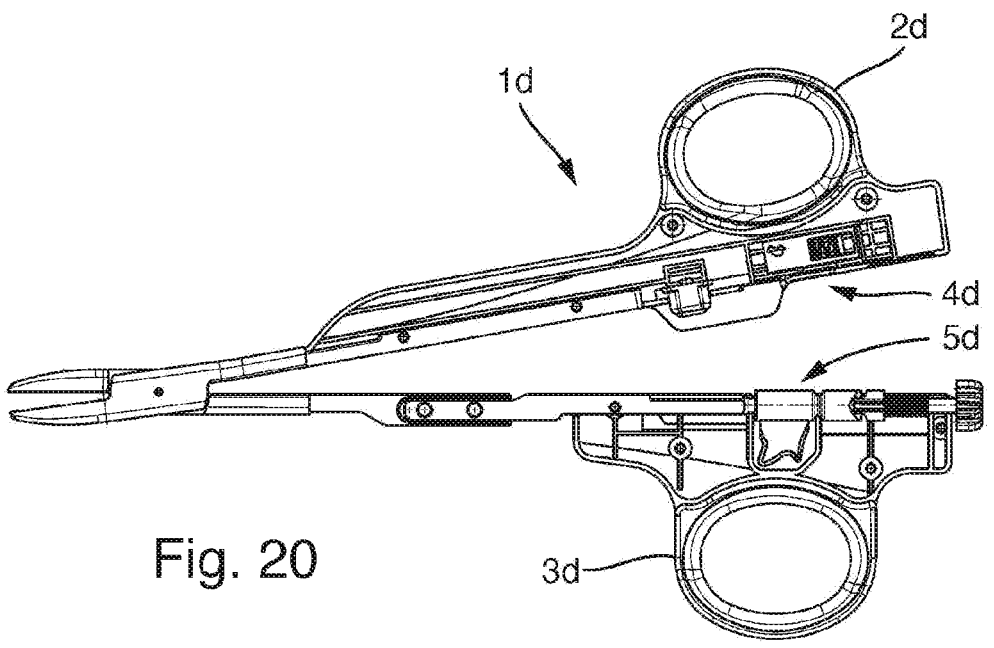
Figure 21:
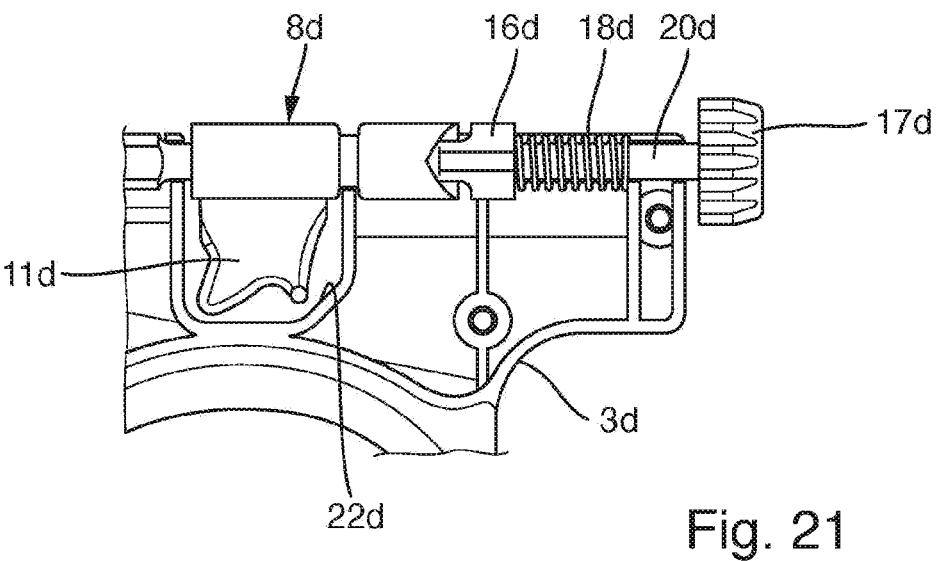
Figure 22:
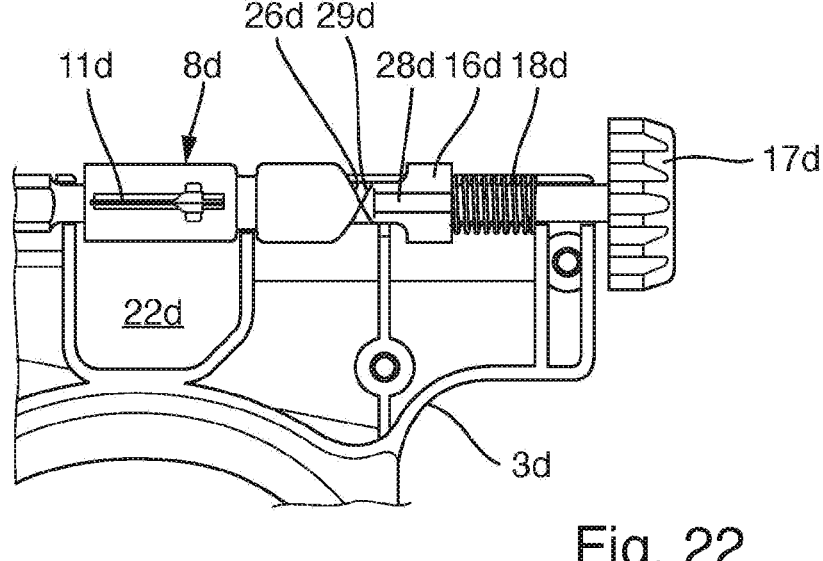
Figure 23:
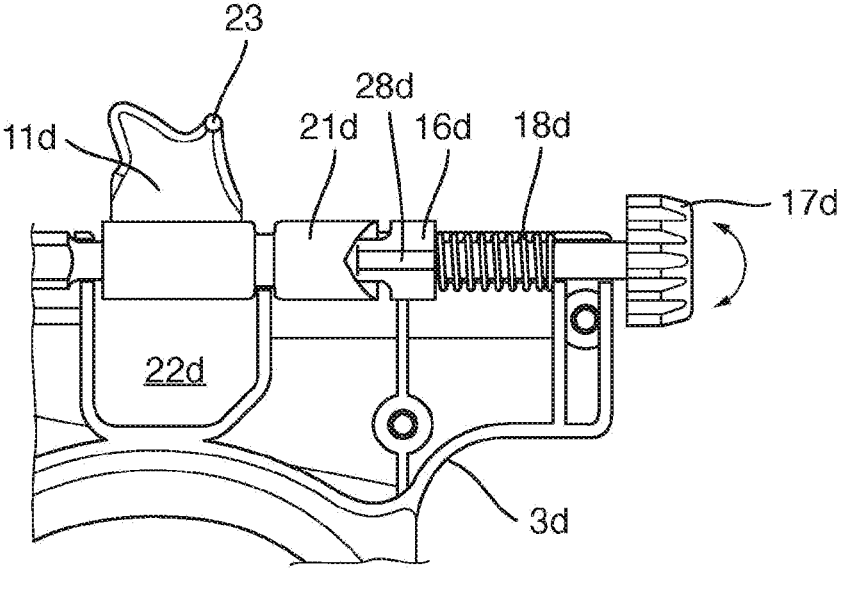
Figure 24:
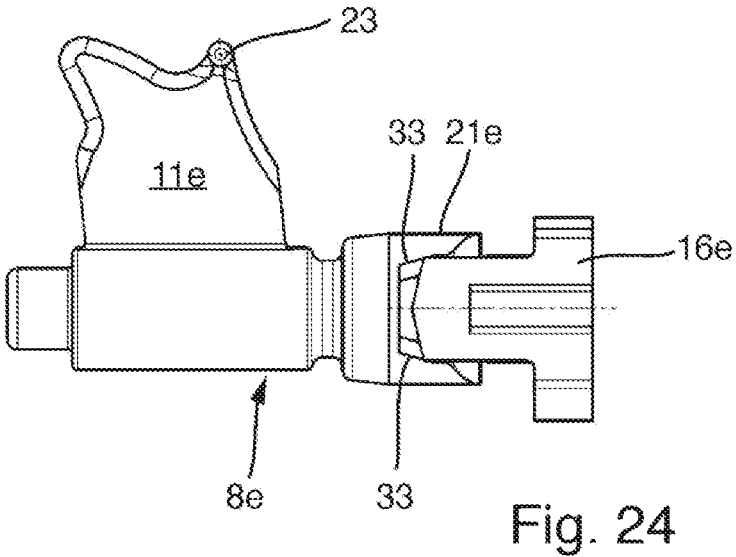
Figure 25:
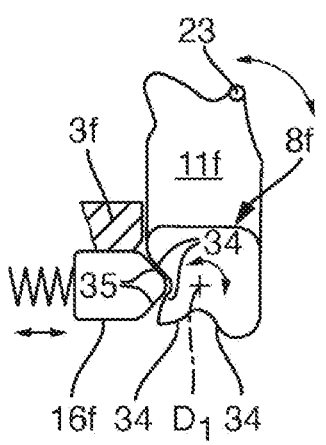
Figure 26:
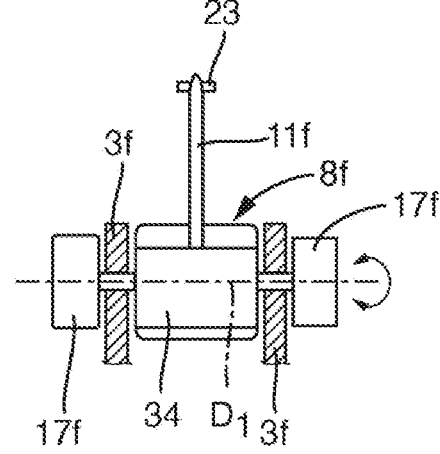

Further advantages and features of the invention can be gathered from the following description of preferred exemplary embodiments of the invention, which are illustrated with reference to the drawings, in which:

FIG. 1 shows a plan view of a first embodiment of a surgical instrument according to the invention, FIG. 2 shows an enlarged illustration of a subregion of the surgical instrument according to FIG. 1, FIG. 3 shows a subregion of a further embodiment of a surgical instrument according to the invention, similar to FIG. 2, FIG. 4 shows a schematically enlarged sectional illustration of a manually operable, form-fit-action securing unit of a catch of the surgical instrument according to FIGS. 1 and 2, FIG. 5 shows the securing unit according to FIG. 4, but omitting a fixed-position linear guide within a gripping limb of the surgical instrument according to FIGS. 1 and 2, FIG. 6 shows the securing unit according to FIG. 5 in a side view which clearly shows an arresting portion of a male arresting arrangement of the catch, FIG. 7 shows, schematically, a subregion of a further embodiment of a surgical instrument according to the invention which is similar to FIG. 2 or FIG. 3, but with a translatory linear guide for an arresting portion of the catch along a circle-arc path, FIG. 8 shows a further embodiment of a surgical instrument according to the invention, this time with a rotary-mounted arresting portion of a male arresting arrangement of a catch, FIG. 9 shows an enlarged perspective illustration of a subregion of the surgical instrument according to FIG. 8 with the male arresting arrangement, FIG. 10 shows a subregion of a gripping limb of the surgical instrument according to FIG. 8 to which the male arresting arrangement is assigned, FIG. 11 shows a further illustration analogous to FIG. 10, FIG. 12 shows a sectional illustration of the subregion according to FIG. 11 taken along section line XII-XII in FIG. 11, FIG. 13 shows the subregion according to FIG. 10, but with the arresting portion in its functional position, FIG. 14 shows a side view of functional components of a positive-control device for the arresting arrangement according to FIGS. 8 to 13, FIG. 15 shows a sectional illustration taken along section line XV-XV in FIG. 14, FIGS. 16a to 16d show different views of a functional component of the positive-control device for the catch according to FIGS. 8 to 15, FIGS. 17a to 17d show different views of a further functional component of the positive-control device for the catch according to FIGS. 8 to 15, FIGS. 18a to 18d show different illustrations of a further functional component of the positive-control device for the catch according to FIGS. 8 to 15, FIGS. 19a to 19d show a manual actuating element for the positive-control device of the catch according to FIGS. 8 to 15, FIG. 20 shows a further embodiment of a surgical instrument according to the invention, with a simplified, rotary-action male arresting arrangement, FIG. 21 shows an enlarged illustration of a subregion of the surgical instrument according to FIG. 20 with the male arresting arrangement, FIGS. 22 and 23 show different functional positions of the arresting arrangement according to FIG. 21, FIG. 24 shows a male arresting arrangement according to a slightly modified embodiment of the invention, and FIGS. 25 and 26 show different illustrations of a further embodiment of a male arresting arrangement according to the invention for a surgical instrument according to one embodiment of the invention.

DETAILED DESCRIPTION

FIGS. 1 to 26 will be used hereinbelow to describe various embodiments of surgical instruments 1 to 1f according to the invention, wherein functionally identical portions or components are given identical reference signs, with the addition—depending on embodiments—of the respective letter a to f. All the embodiments according to FIGS. 1 to 26 have two gripping limbs 2, 3 (plus the corresponding letter variant), which can be pivoted relative to one another in a common pivoting plane and are mounted such that they can be pivoted relative to one another for complementary movement of two clamping jaws. The two gripping limbs 2, 3 are assigned a catch, which allows the two gripping limbs 2, 3 to be arrested relative to one another in a releasable manner in order to retain, in particular, the two clamping jaws in a clamping position. In all the embodiments, the catch has a female arresting arrangement 4 and a male arresting arrangement 5 (plus the variants, which can be differentiated by letter). In all the embodiments illustrated and described hereinbelow, the female arresting arrangement 4, 4a, 4c, 4d is configured in a manner identical to the female arresting arrangement as is described in more detail and illustrated in DE 10 2016 118 199 A1, in particular in FIGS. 6 to 11. Accordingly, the female arresting arrangement has an arresting carriage, which can be displaced in a linearly movable and spring-assisted manner in the longitudinal direction of the gripping limb 2, 2a, 2c, 2d and is provided with a control track 28, in which a control cam 23 of an arresting portion 11 to 11f of a male arresting arrangement engages. The arresting carriage can be slid in a linearly movable manner, under spring loading, along a longitudinal direction of the gripping limb 2d. The control cam of the arresting portion of the male arresting arrangement 5 to 5f interacts with the control track 28 of the arresting carriage of the female arresting arrangement 4 to 4d in line with a heart-shaped curve in a manner analogous to the ballpoint-pen principle, wherein the control or latching cam 23 of the arresting portion of the male arresting arrangement 5 to 5f slides along corresponding control contours of the control track 28, with the arresting carriage being displaced transversely in the process, until the control or latching cam ends 23 up in abutment in a latching mount of the control track 28. In this position, the catch 23 is in the arrested state. The arresting portion of the male arresting arrangement reaches this position by the gripping limbs 2, 3 being pushed together manually toward one another. As a result of them being briefly pushed together again, the control or latching cam 23 of the arresting portion of the male arresting arrangement 5 passes into the release path of the control track 28, as a result of which the arresting portion comes free again and the two gripping limbs 2, 3 can be separated from one another and pivoted apart from one another. This unavoidably results in the two clamping jaws also moving apart from one another, and these are therefore transferred again from the clamping position into the freeing position.

The embodiments which will be described hereinbelow differ from one another exclusively in terms of the configuration and control of the male arresting arrangement. The surgical instruments according to FIGS. 1 to 7 here are embodiments in which the arresting portions of the male arresting arrangements are mounted for translatory movement between their different end positions. In contrast, the embodiments according to FIGS. 8 to 26 are embodiments of surgical instruments in which the respective arresting portion of the male arresting arrangement can be displaced in each case in rotary fashion between its end positions, that is to say a rest position and a functional position. The individual embodiments will be described in detail hereinbelow. All the embodiments have guiding crosspieces 6 (see, in particular, FIG. 2) in the region of the mutually facing sides of the gripping limbs, and these guiding crosspieces stabilize the catch against the influences of transverse forces.

The surgical instrument 1 according to FIGS. 1, 2, 4, 5 and 6 has a male arresting arrangement 5 in which an arresting portion 11, which projects in the form of a crosspiece or tongue from the gripping limb 3, can be displaced by means of a control arrangement 8 between a functional position according to FIGS. 1 and 2 and an end position which defines a rest position. The control arrangement 8 has a control carriage, on which the arresting portion 11 is arranged in a fixed state with its control or latching cam 23 (FIG. 6). The control carriage is guided, with the aid of column-like guides 14, in a rectilinear linear guide 9 in the longitudinal direction of the gripping limb 3, which runs parallel to an edge region which is directed toward the opposite gripping limb 2. The linear guide 9 is formed by guide grooves in two housing shells of the gripping limb 3, wherein, to give a better overview, an upper housing shell has been omitted from FIGS. 1 and 2. A guide groove is additionally provided for the arresting portion 11, in a manner which is not illustrated specifically, in the edge region which is directed toward the opposite gripping limb 2, and the edges of this guide groove flank the arresting portion 11 on both sides in order to support the same against any transverse forces which occur. The control carriage of the control arrangement 8 is subjected to permanent spring loading by a spring device 10, in this case in the form of a helical compression spring, in the direction of its end position which forms the rest position, that is to say in the direction of a proximal end of the gripping limb 3. In an embodiment of the invention which is not illustrated, the spring device is active in the opposite direction, i.e. in the direction of the end position which forms the functional position. In order to be able to arrest the arresting portion 11 in the functional position according to FIGS. 1 and 2, the control arrangement 8 has securing means in the form of a latching arrangement, and the securing means are formed by two elastically movable latching noses 13 and complementary latching apertures 14 in the gripping limb 3. The latching apertures 14 are provided in fixed position in the region of the linear guide 9 in the gripping limb 3. The latching apertures 14 are positioned such that, once the latching noses 13 have latched into the latching apertures 14, the arresting portion 11 is located in the functional position, in which it can interact with the female arresting arrangement 4 when the gripping limbs 2 and 3 are pushed together, in order to arrest the catch. Sliding elements, which are not designated in any more detail, are assigned to the control arrangement 8, on opposite sides of the gripping limb 3—in the illustration according to FIG. 2, in the region of an upper side and in the region of an underside—these sliding elements being arranged in the fixed state on the control carriage of the control arrangement 8. Arranged in the fixed state can be understood to mean a single-piece formation or a force-fitting or form-fitting or integral connection. The sliding elements are parts of a manually operable actuating device, which is provided to release the securing means. The sliding elements are assigned actuating cams 12, which are arranged in an elastically movable manner and can interact with the latching cams 13 of the control carriage 8. Simply pushing the actuating cams 12 inwards, in particular at the same time, unavoidably results in the latching cams 13 also being pushed inward, in which case the latter come free from the latching apertures 14 and the spring device 10 can unavoidably push the control carriage into the proximal end position of the linear guide 9. The effective length of the spring device 10 is coordinated with the maximum distance which can be covered by the control arrangement 8 within the linear guide 9 in such a manner that the control carriage of the control arrangement 8 is subjected to spring loading by the spring device 10 in any position. A return of the control arrangement 8 from the proximal end position, which forms the rest position, into the end position which is illustrated in FIGS. 1 and 2, and forms the functional position, takes place manually by the sliding elements being gripped and the control arrangement 8 being slid, counter to the force of the spring device 10, until the latching cams 13 of the control arrangement 8 have reached the latching apertures 14 again, the latching cams 13 latching automatically into the latching apertures 14 and therefore securing the arresting portion 11 in this functional position.

For the surgical instrument 1*a* according to FIG. 3, functionally identical portions and components are provided with identical reference signs, but with the addition of the letter a. In order to avoid repetition, reference is therefore made, in addition, to what has been said in relation to the embodiment according to FIGS. 1, 2 and 4 to 6. Details will be given hereinbelow merely of the differences between the surgical instrument 1*a* and the embodiment described above. It is also the case with this embodiment that sliding elements are provided as parts of a manually operable actuating device.

The key difference for the surgical instrument 1*a* is that a form-fit-action securing means is replaced by a force-fit-action securing means for the arresting portion 11*a* in the end position which defines the functional position. For this purpose, at the end position which defines the functional position, the gripping limb 3*a* has a small shell-like depression 7 in the region of the linear guide 9*a*. The control arrangement (not designated in any more detail) with its control carriage, which carries the arresting portion 11*a*, and being subjected to the compressive action of the spring device 10*a*, has a complementary, stud-like profiling, which can penetrate into the depression 7 with frictional locking and thus gives rise to the arresting portion 11*a* being secured in the functional position under certain force limits. The restraining force caused by this frictionally locking securing action is higher than the compressive force of the spring device 10*a*, but at the same time lower than a force which can be applied manually in order for it to be possible, by the sliding elements of the actuating device being gripped, to slide the arresting portion 11*a* in the direction of the proximal end position. The transfer of the arresting portion 11*a*, following overriding of the frictionally locking securing action in the functional position, into the proximal end position takes place unavoidably by way of corresponding loading of the spring device 10*a* in a manner analogous to the embodiment described above.

In the embodiment according to FIG. 7, the arresting portion 11*b* of the male arresting arrangement can likewise be slid in a translatory fashion. In a manner which is not illustrated specifically, the arresting portion 11*b* is assigned a force-fit-action or form-fit-action securing means, as has been disclosed with reference to the embodiments described above, for the functional position, which is illustrated on the left in FIG. 7. In order to avoid repetition, reference is therefore likewise made in this respect to the corresponding disclosure relating to the preceding embodiments. The crucial difference of the embodiment according to FIG. 7 is that the linear guide 9*b* in the gripping limb 3*b*, rather than being rectilinear, extends along a circle arc in the pivoting plane of the gripping limb 3*b*. A center point of this circle arc is illustrated schematically in FIG. 7. At the proximal end, an edge region of the gripping limb 3*b* that is directed toward the opposite gripping limb has a pocket (not designated in any more detail), into which the arresting portion 11*b* can penetrate when it is being transferred into the proximal end position. In this proximal end position, the arresting portion

11*b* is arranged within the outer contours of the gripping limb 3*b*, so that its region which projects in the form of a tongue or crosspiece, and is provided with the control or latching cam, no longer protrudes beyond the edge region of the gripping limb 3*b*. This means that in particular a glove worn by a person operating the surgical instrument cannot get caught on the arresting portion 11*b* in the rest position of the arresting portion 11*b*. It is also the case with this embodiment that the spring device 10*b* is part of the control arrangement which, once the arresting portion 11*b* has been released from its functional position, unavoidably transfers the arresting portion 11*b* into the end position which defines the rest position.

In the embodiments according to FIGS. 8 to 26, the respective arresting portion 11*c* to 11*f* is displaced in rotary fashion between its two end positions, which define the functional position and the rest position. For the surgical instrument 1*c* according to FIGS. 8 to 19*d*, in addition, the arresting portion 11*c* is assigned a positive-control device, which will be described in more detail hereinbelow and is configured such that the arresting portion 11*c*, rather than being able to remain in an intermediate position, always unavoidably pivots, under the action of spring force, into one of the two end positions. In addition, the positive-control device according to FIGS. 8 to 19*d* is assigned, in the manner described hereinbelow, a time-delay unit, which only acts on the arresting portion 11*c* when relatively large control movements are involved. This ensures that the arresting portion 11*c* remains in its end position, in particular when any transverse forces occur. In all the embodiments, functionally identical parts and portions are provided with identical reference signs, with the addition of distinctive lower-case letters. In order to avoid repetition, reference is additionally made in each case to the other embodiments described.

The male arresting arrangement of the surgical instrument 1*c* according to FIGS. 8 to 19*d* is mounted in the gripping limb 3*c* such that it can be rotated in rotary fashion about an axis of rotation D by way of a rotary bearing means, wherein the axis of rotation D runs at least largely in the longitudinal direction of the gripping limb 3*c*, as can be seen with reference to FIGS. 10 and 11. A control arrangement 8*c* forms a rotatable body, which is mounted in a rotatable manner in corresponding bearing locations of the gripping limb 3*c* (see, in particular, FIG. 9). The bearing locations flank a through-passage 22 of the gripping limb 3*c*, the through-passage being formed both in an upper housing shell (not illustrated) and in a lower housing shell of the gripping limb 3*c*, the lower housing shell being clearly visible in FIG. 9. The through-passage 22 is open toward the adjacent gripping limb 2*c*, as can be seen with reference to FIG. 8. The crosspiece-form or tongue-form arresting portion 11*c*, which is formed in one piece on the rotary body of the control arrangement 8*c*, projects radially from the body of the control arrangement 8*c*. The arresting portion 11*c* has the control or latching cam 23*c*, which has already been described above in respect of function. The through-passage 22 therefore allows the arresting portion 11*c* to be rotated by 360° about the axis of rotation D through the gripping limb 3*c*. The control arrangement 8*c* is assigned a positive-control device, which will be described in more detail hereinbelow and serves to guide the arresting portion 11*c* always into one of its two end positions, that is to say the functional position, in which it is directed toward the opposite gripping limb 2*c*, or the rest position, in which it is accommodated in the through-passage 22, and to retain it there. A plurality of functional components are provided for this purpose, and are illustrated more specifically with reference to FIGS. 16*a* to 19*d*. At its proximal end, the control arrangement 8*c* has a control mouth 21, which is provided on the end side with control contours 26 which slope up and slope down in helical form in the circumferential direction, as can be seen, in particular, with reference to FIGS. 16*a* to 16*d*. In addition, the control mouth 21 has, on the inside, a total of four control stops 24, which are offset in relation to one another in the circumferential direction. The helical control contours 26 are provided on the end side of two extensions which are located radially opposite one another and extend axially toward the proximal end of the gripping limb 3*c*, wherein the control contours 26 slope up at equal angles, but in opposite directions, in relation to one another, so that a central prominence is formed on each of the opposite extensions. In addition, the control mouth 21 has on the inside, coaxially in relation to the axis of rotation D, a cylindrical mount, in which a cylindrical distal end of an actuating rod 20 (see FIGS. 18*a* to 18*d*) is mounted for relative rotation. A proximal end of the actuating rod 20 is provided with a square stub 32, onto which an actuating element 17 in the form of a rotary knob can be fitted in a rotationally locking manner (FIGS. 19*a* to 19*d*). In further embodiments of the invention which are not illustrated, the end is provided with a different, rotationally non-symmetrical configuration, onto which the actuating element can be fitted in a rotationally locking manner. The actuating element 17 has a complementary square aperture 31, which ensures that the actuating element 17 is fitted in a rotationally locking manner onto the proximal end of the actuating rod 20 and therefore onto the square stub 32. As can be seen with reference to FIGS. 8 to 11 and 13, the actuating element 17 is mounted in a rotatable manner in the gripping limb 3*c*, coaxially in relation to the axis of rotation D, in the region of a bearing location at a proximal end of the gripping limb 3*c*.

The control arrangement is additionally assigned a control slide 16 (see FIGS. 17*a* to 17*d*), which is mounted such that it can be slid in translatory fashion in a linear guide 19, which is merely indicated in the drawings, coaxially in relation to the axis of rotation D. The control slide 16 is permanently subjected to the action of a spring device 18, in the form of a helical compression spring, which surrounds the actuating rod 20, is supported in a fixed position, proximally, in the region of the bearing location for the actuating element 17 and is supported, distally, on an end side of the control slide 16 in order to subject the latter permanently, in the longitudinal direction of the axis of rotation D, to a compressive spring force. The control slide 16 encloses the actuating rod 20 in a hollow-cylindrical manner and, accordingly, can be slid in a linearly movable manner, within limits, relative to the actuating rod 20. The actuating rod 20, in turn, is mounted in a rotatable manner, coaxially in relation to the axis of rotation D, within the control slide 16. All the functional components—that is to say the control arrangement 8*c* with the control mouth 21, also the control slide 16, the actuating rod 20, the spring device 18 and the actuating element 17—can be assembled relative to one another, ready for operation, simply by being fitted together, without any additional fixing means being required. The actuating element 17 and the actuating rod 20 form a manually operable actuating device along the lines of the invention. Depending on the embodiment, the spring device 18 has a linear or progressive characteristic, this being dependent on how the rest of the functional components interact in terms of their positive-control function and their time-delay function for the arresting portion 11*c*.

As can be seen with reference to FIGS. 18*a* to 18*d*, the actuating rod 20 has on opposite sides, in the region of its cylindrical outer circumference, a respective integrally formed control attachment, wherein each of the two control attachments is formed by a respective longitudinally extending control cam 25 and a control wedge 27, which adjoins the control cam 25 in the proximal direction and is provided, proximally, with control contours which slope up and slope down in the opposite direction in helical form in the circumferential direction. The oppositely directed control contours form a prominence in a manner analogous to the control mouth 21. The corresponding prominence is directed, proximally, toward the square-stub end 32 of the actuating rod 20, so that the two diametrically opposite control attachments have parallel, distally oriented control cams 25 and proximally oriented control wedges 27.

As can be seen with reference to FIGS. 17*a* to 17*d*, the control slide 16 has, in a manner analogous to the control mouth 21 of the control arrangement 8*c*, two control extensions which project in mouth form and are provided on the end side with control contours 29 which slope up and slope down axially in helical form, in a manner analogous to the control contours 26 of the control mouth 21. It is also the case that the control contours 29 of the extensions of the control slide 16 each form, in pairs, a prominence in a manner analogous to the control mouth 21 of the control arrangement 18. In addition, offset by 90° in the circumferential direction and set back axially in relation to the extensions with the control cams 29, the control slide 16 has two further pairs of control cams 30, which are positioned on a circumferential line which is further inward, in the radial direction, than the control cams 29. It is also the case that these pairs of control cams 30, located opposite one another, each form a prominence, which is flanked by a control contour which slopes up axially in the circumferential direction and a control contour 30 which slopes down axially in the same circumferential direction. As seen in the radial direction, these control contours 30 are provided on the same circumferential line as the control wedges 27 of the actuating rod 20.

In the assembled operating state, the control contours of the two control wedges 27 of the actuating rod 20 and the radially inner control contours 30 of the control slide 16 are directed toward one another and in contact with one another. In addition, the radially outer control contours 29 of the control slide 16 and the control contours 26 of the control mouth 21 are located on the same circumferential line and therefore, depending on position, are in contact with one another. The correspondingly diametrically opposite, mouth-like extensions of the control mouth 21 and of the control slide 16 are directed counter to one another, so that the control slide 16 and the control mouth 21 can penetrate axially one inside the other after having been rotated relative to one another at least largely at right angles. The arresting portion 11*c* is thereby fixed in terms of rotation. In addition, the control cams 25 of the actuating rod 20 interact with the control stops 24 of the control mouth 21. Since the spring device 18 permanently applies a translatory compressive force to the control slide 16 distally in relation to the gripping limb 3*c*, the control slide 16 and the control mouth 21 of the control arrangement 8*c* are permanently in contact with one another. This gives rise to two stable end positions, in which the diametrically opposite extensions of the control slide 21, on the one hand, and also of the control mouth 21 engage axially one inside the other. Since the control slide 16 with its mouth-like extensions can only be slid in translatory fashion and, accordingly, is always subjected to spring force along the axis of rotation D, the control mouth 21 penetrates between these extensions of the control slide 16 such that the arresting portion 11c is rotated either into its rest position according to FIG. 11 or into its functional position according to FIG. 13. Accordingly, the two end positions are achieved in each case by the control arrangement 8c, and therefore the control mouth 21, being rotated by 180°. The respectively abutting control contours with their central prominences ensure, in conjunction with the permanent compressive force of the spring device 18, that the arresting portion 11c is never in an unstable state. The control contours unavoidably slide relative to one another in the circumferential direction either in one direction or the other, until the mouth-like extensions of the control mouth 21 and of the control slide 16 engage axially one inside the other in a stable state in one of the two end positions. The positive control brought about by the control contours is initiated by a rotary movement of the actuating element 17 in any desired direction of rotation. Since the control cams 25 run freely relative to the control stops 24 of the control mouth 21 over a certain angle range in both directions of rotation before they come into contact with one another in the circumferential direction, it is not possible for small rotary movements of the actuating element 17, in particular ranging between 5° and approximately 85°, to trigger any activation of the rotary movement of the arresting portion 11c. It is only when the actuating element 17 is rotated to the extent (by at least approximately 90°) where the control cams 25 strike against the control stops 24 of the control mouth 21 in one direction of rotation or the other that the arresting portion 11c is correspondingly subjected to torque and rotated. Once rotary movement of the arresting portion 11c has been initiated, there is no need for the rotary movement of the actuating element 17 to be completed in order for the arresting portion 11c to be rotated into the corresponding end position. Rather, once the respective prominences have slid past one another in the circumferential direction, the corresponding control contours of the functional components described unavoidably slide relative to one another, on account of the permanent driving force supplied by the spring device 18, until the other stable end position between the control slide 16 and the control mouth 21 of the control arrangement 8c has been reached. Accordingly, it is never possible for the arresting portion 11c to remain in an unstable intermediate position. Rather, the positive-control device always results in the arresting portion 11c either remaining in the end position which has already been set or being transferred into the opposite end position, that is to say the end position in which the arresting portion is rotated by 180°.

In the embodiment according to FIGS. 8 to 19d, corresponding gradients of the inner and outer control contours of the mouth-like extensions of the control slide 16, on the one hand, and the control contours of the control wedges 27 of the actuating rod 20 and also the control contours 26 of the control mouth 21, on the other hand, can be provided with different gradients, so as to avoid jamming or blocking resulting from corresponding self-locking of the control contours when they are supported on one another. In addition, the corresponding gradients can be coordinated with the characteristic of the spring device 18, in order for reliable transfer into the respective end position to be achieved and for mechanical noises to be triggered as a deliberate measure when the end position is reached.

In order to allow for circumferentially play-free positioning for the arresting portion 11c in the two end positions, provision is made, in a variant of the surgical instrument 1c as is illustrated in FIG. 24, for the control mouth 21 to be provided with centering slopes 33 in the region of the apertures into which the mouth-like extensions of the control slide 16 penetrate. As an alternative, or in addition, it is also, of course, possible for the complementary abutment surfaces of the control slide 16e to be provided with run-on slopes in order to achieve the centering action, and accordingly the circumferentially play-free positioning, between the control mouth 21e and the control slide 16e.

The surgical instrument 1d according to FIGS. 20 to 23 corresponds largely to the above-described surgical instrument 1c according to FIGS. 8 to 19d. In order to avoid repetition, reference is therefore made, in addition, to the embodiment described above. The key difference is that the male arresting arrangement 5d of the surgical instrument 1d does not have a time-delay unit, as is provided in the embodiment according to FIGS. 8 to 19d. Accordingly, the male arresting arrangement 5d is, indeed, likewise of rotary configuration, but it is of more straightforward design than the arresting arrangement 5c according to FIGS. 8 to 19d. Therefore, where the surgical instrument 1d is concerned, rotation of the actuating element 17d unavoidably leads directly to rotation of the arresting portion 11d. In addition, torques acting on the arresting portion 11d lead directly to corresponding relative rotation of the arresting portion 11d. Accordingly, fixing of the arresting portion in the respective end position is absent from this embodiment, in contrast to the embodiment described above. Otherwise, the positive-control device for rotating the arresting portion 11d between the two end positions is of functionally identical design to the above-described embodiment according to FIGS. 8 to 19d. Functionally identical parts and portions are therefore provided with identical reference signs, but with the addition of the letter d. In order to avoid repetition, reference is therefore made, in addition, to the disclosure relating to FIGS. 8 to 19d.

The positive-control device merely requires control contours in the region of the mouth-like extensions of the control slide 16d, on the one hand, and of the control mouth 21d, on the other hand, that can slide on one another in one direction of rotation or the other in order to be able to rotate the arresting portion 11d into one end position or into the other end position, and in order to avoid unstable intermediate positions of the arresting portion 11d. In this embodiment, the arresting portion 11d, including the control mouth 21d, is connected for conjoint rotation to the actuating element 17d, which is designed in the form of a rotary knob. The control slide 16d serves merely to fix the arresting portion 11d in either one of the two end positions and in addition, by corresponding sliding of the control contours, to subject the control mouth 21d at all times to a torque in one of the two directions of rotation, until the extensions of the control slide 16d and of the control mouth 21d engage axially one inside the other in a stable state and, accordingly, any further rotation in the circumferential direction is ruled out. Rotation of the actuating element 17d unavoidably causes rotation of the control mouth 21d, which forces the control slide 16d back, via the corresponding control contours, counter to the compressive force of the spring device 18d until the prominences of the two functional components slide past one another. There is then no longer any need for the actuating element 17d to be subjected to any further manual rotary movement, since the control slide 16d, via the control slopes, unavoidably rotates the control mouth 21d into the correspondingly opposite end position, rotated by 180°, and circumferentially secures the same in this end position.

FIGS. 25 and 26 show, schematically, a further embodiment of a male arresting arrangement for a surgical instrument, which is configured in a manner similar to the embodiments described above. The key factor for this embodiment is that, although the arresting portion 11*f* is likewise mounted in rotary fashion about the axis of rotation $D_1$, this axis of rotation $D_1$ is oriented orthogonally in relation to the pivoting plane of the gripping limbs. In contrast, the axis of rotation D of the above-described embodiments according to FIGS. 8 to 24 is located either in the pivoting plane of the gripping limbs 2, 3 or parallel to this pivoting plane. It can be seen with reference to the illustrations in FIGS. 25 and 26 that this embodiment also has a positive-control device, wherein a corresponding control body, to which the arresting portion 11*f* is connected for conjoint rotation, is mounted within the gripping limb 3*f* such that it can be pivoted, within limits, about the axis of rotation $D_1$. A control wedge 16*f*, which serves as control element, is subjected to the action of a spring device and is mounted within the gripping limb 3*f* such that it can be moved in translatory fashion, within limits, in the direction of the double arrow in FIG. 25. In the region of its outer side, which is directed toward the control wedge 16*f*, the control body 8*f*, which is part of a control arrangement along the lines of the invention, has a plurality of control contours 34 which have, on the one hand, latching pockets for securing the two end positions of the arresting portion 11*f*, these end positions being offset in relation to one another by 90°, and, on the other hand, a prominence, over which a complementary prominence of the control wedge 16*f* slides so as to provide for the arresting portion 11*f* pivoting in stable fashion into the respectively other end position. The gripping limb 3*f* is provided, in a manner which is not illustrated specifically, with an aperture or pocket, into which the arresting portion 11*f* can penetrate in its end position which defines the rest position. This end position is rotated by 90° in relation to that end position of the arresting portion 11*f* which is illustrated in FIGS. 25 and 26, and defines the functional position. Coaxially in relation to the axis of rotation $D_1$, rotary actuating elements 17*f*, in this case in the form of rotary knobs, are provided on opposite outer sides of the gripping limb 3*f*, these rotary actuating elements being connected to the control body 8*f* in a rotationally locking manner in each case and being mounted in a rotatable manner in the gripping limb 3*f* in the bearing locations for the control body 8*f*. This is clearly shown by the double arrow which can be seen on the right-hand side of FIG. 26. The arresting portion 11*f* also has a control or latching cam 23, as is the case with the embodiments described above. Accordingly, this control or latching cam 23 interacts, in the manner described above, with the female arresting arrangement (not illustrated).

The invention claimed is:

1. A surgical instrument comprising:
a first gripping limb;
a second gripping limb movable relative to the first gripping limb; and
a catch configured to arrest the first gripping limb and the second gripping limb relative to one another in a releasable manner, wherein the catch has a female arresting arrangement in a region of the first gripping limb and a male arresting arrangement in a region of the second gripping limb, wherein the female arresting arrangement is configured to selectively connect to the male arresting arrangement, a mechanical control arrangement configured to displace the arresting portion of guide the male arresting arrangement from a first end position that defines a rest position into a second end position that defines a functional position and from the second end position that defines the functional position into the first end position that defines the rest position, and wherein the mechanical control arrangement comprises:
a guide groove formed in the second gripping limb and extending from the first end position to the second end position, and having latching apertures located at the second end position,
a carriage secured to the male arresting arrangement, the carriage being located within and movable within the guide groove along a travel path extending between the first end position and the second end position,
latching cams elastically secured to opposite lateral sides of the carriage and extending in opposite lateral directions away from the travel path, wherein the latching cams are elastically biased into the latching apertures when the male arresting arrangement is in the second end position,
sliding elements secured to the opposite lateral sides of the carriage and located outside the guide groove, each sliding element comprising an actuating cam that is located adjacent to a respective one of the latching cams, wherein the actuating cams are movable transverse to the travel path to press the respective latching cams out of the latching apertures to allow the carriage to move from the second end position towards the first end position.

2. The surgical instrument according to claim 1, wherein the travel path is straight.

3. The surgical instrument according to claim 1, wherein the travel path is curved.

4. The surgical instrument according to claim 1, wherein latching cams comprise form-fit-action securing units.

5. A surgical instrument comprising:
a first gripping limb;
a second gripping limb movable relative to the first gripping limb; and
a catch configured to arrest the first gripping limb and the second gripping limb relative to one another in a releasable manner, wherein the catch has a female arresting arrangement in a region of the first gripping limb and a male arresting arrangement in a region of the second gripping limb, wherein the female arresting arrangement is configured to selectively connect to the male arresting arrangement, a mechanical control arrangement configured guide the male arresting arrangement from a first end position that defines a rest position into a second end position that defines a functional position and from the second end position that defines the functional position into the first end position that defines the rest position, and wherein the mechanical control arrangement has securing means that are provided to secure the male arresting arrangement in at least one of the first end position and the second end position, and wherein the mechanical control arrangement comprises a groove configured to guide the male arresting arrangement along a curved path.

* * * * *